United States Patent [19]
Chang

[11] Patent Number: 6,047,830
[45] Date of Patent: Apr. 11, 2000

[54] RETAINER FOR RECEIVING KNIVES AND CUTTING BOARDS

[76] Inventor: Yuan Fu Chang, No. 70, Lane 125, Feng-Nien Rd, Feng-Yuan City, Taichung, Taiwan

[21] Appl. No.: 09/311,871

[22] Filed: May 14, 1999

[51] Int. Cl.[7] .................................................. B65D 71/00
[52] U.S. Cl. .......................................... 206/576; 206/372
[58] Field of Search .................................... 206/349, 372, 206/373, 207, 213.1, 205, 216, 223, 576

[56] References Cited

U.S. PATENT DOCUMENTS 5,660,311  8/1997  Soltau ................................. 206/371 X
5,676,240  10/1997  Cziraky et al. ..................... 206/373 X Primary Examiner—Jacob K. Ackun
Attorney, Agent, or Firm—Charles E. Baxley, Esq.

[57] ABSTRACT

A retainer for receiving knives and cutting boards includes a base having a bottom with a top plate, a lower plate and two side plates. A cover has two lugs extending therefrom which are pivotally connected to the two side plates of the base. A sanitizing bulb is attached to the inside of the top plate and an outlet is defined through the lower plate wherein a collection box is connected to the lower plate and communicates with the outlet. A rack is connected to the bottom of the base and has a plurality of slots defined therein for the knives and the cutting boards being received therein.

7 Claims, 3 Drawing Sheets

RETAINER FOR RECEIVING KNIVES AND CUTTING BOARDS

FIELD OF THE INVENTION

The present invention relates to a retainer for receiving knifes and cutting boards, and more particularly, to a retainer having a rack for the knifes and cutting boards being supported thereon and sanitizing bulbs connected to the top of the retainer to sanitize the knifes and cutting boards.

BACKGROUND OF THE INVENTION

Conventionally, the cutting boards and the knifes used in a kitchen are supported by a rack attached on the wall, or connected to a closet or the like. The cutting boards and the knifes are therefore dried naturally when the water drops attached thereon drop down. Nevertheless, sanitary problems are raised and worried because it takes a long time for the knifes and cutting boards being dried naturally. Although the user may wipe the water drops on the knifes and cutting boards by a fabric, the sanitary problems with regard to the fabric are still existed.

The present invention intends to provide a retainer which has a rack connected between the base and cover of the retainer for the knifes and cutting boards being supported therein, and at least one sanitizing bulb attached to the inside of the base to sanitize the knifes and cutting boards. An outlet is defined in the lower end of the base so as to collect the water drops dropping from the knifes and cutting boards.

By the retainer of the present invention, the knifes and cutting boards are well treated and always kept in a good sanitary status.

SUMMARY OF THE INVENTION

In accordance with one aspect of the present invention, a retainer is provided and comprises a base having a bottom with a top plate and a lower plate respectively extending laterally from two opposite sides thereof and two side plates respectively extending laterally from the other opposite sides of the base. A sanitizing bulb is attached to the inside of the top plate and an outlet is defined through the lower plate. A rack is connected to the bottom of the base and has a plurality of slots defined therein for receiving hives and cutting boards therein.

A first cover is pivotally connected to the base and a collection box is connected to the lower plate and communicates with the outlet.

The primary object of the present invention is to provide a retainer for receiving the knives and the cutting boards, wherein a rack is connected between a base and a cover of the retainer and a sanitizing bulb is connected to the base and an outlet is defined through the lower plate for collecting the water drops attached to the knives and the cutting boards.

Another object of the present invention is to provide a retainer for receiving the knives and the cutting boards wherein the retainer has a sanitizing bulb connected therein.

Further objects, advantages, and features of the present invention will become apparent from the following detailed description with appropriate reference to the accompanying drawings.

DETAILED DESCRIPTION OF THE PREFERRED EMBODIMENTS

Figure 1:
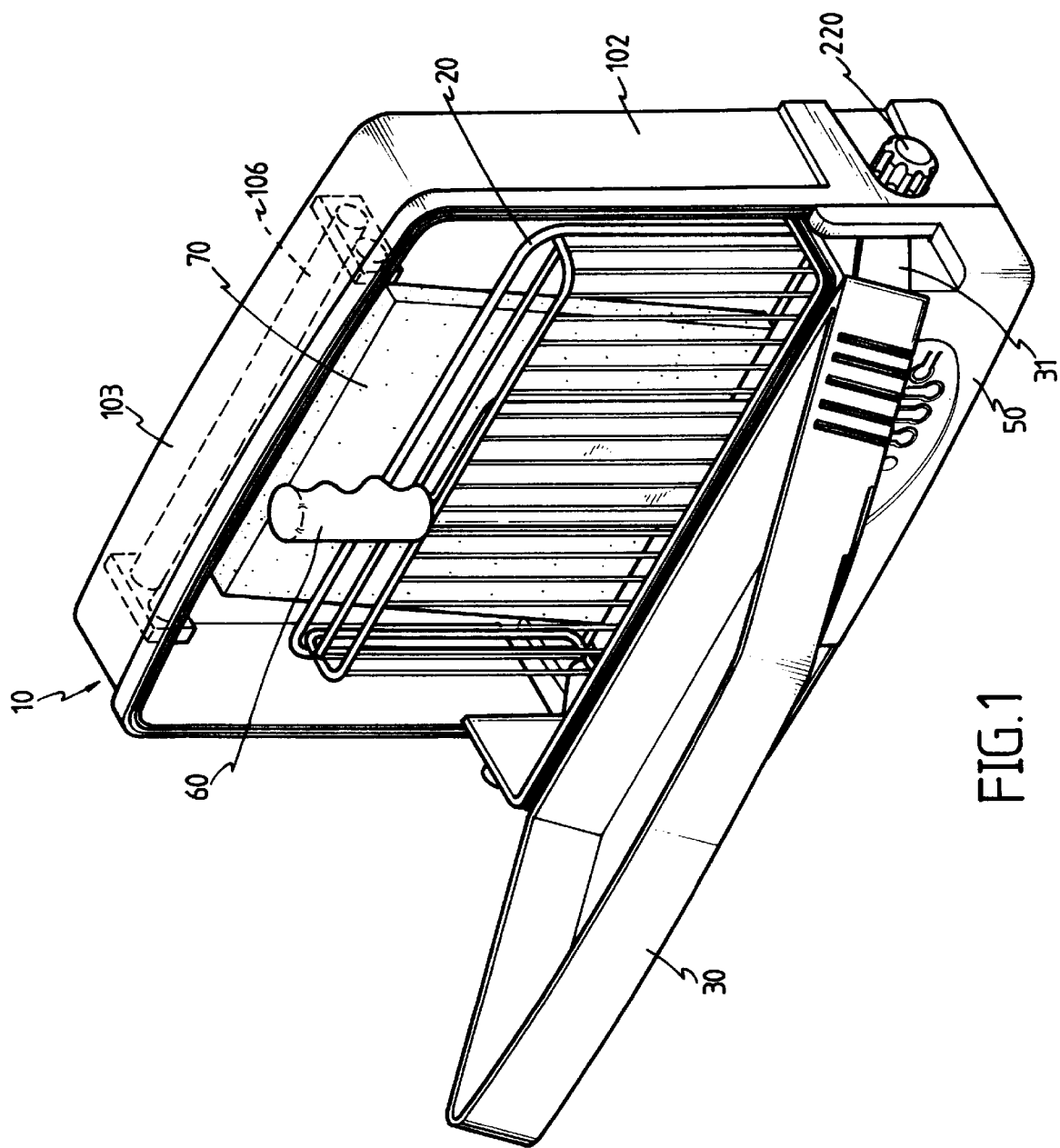
FIG. 1 is a perspective view of the retainer in accordance with the present invention.
Figure 2:
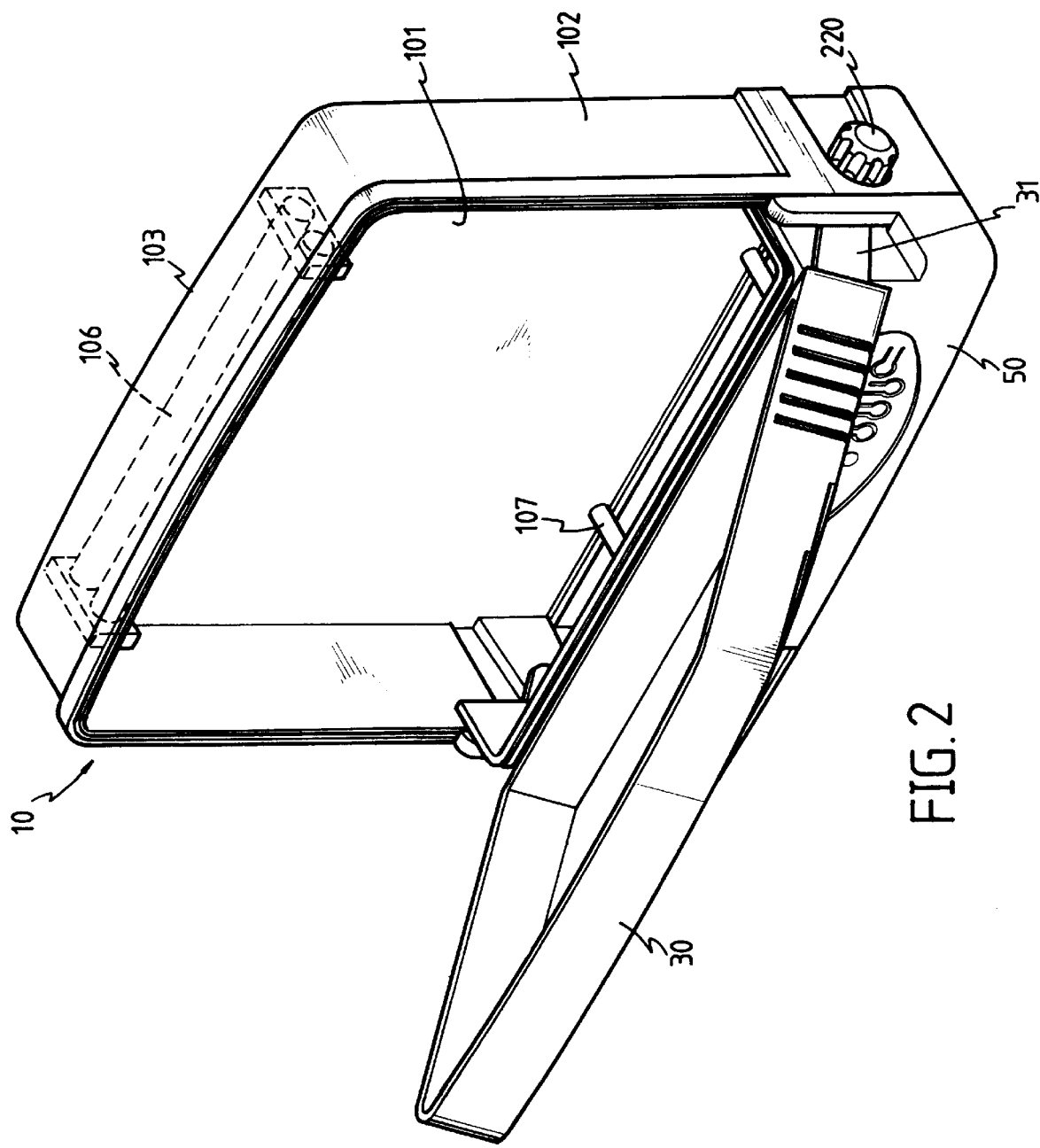
FIG. 2 is a perspective view of the retainer in accordance with the present invention wherein the rack is not yet installed in the retainer.
Figure 3:
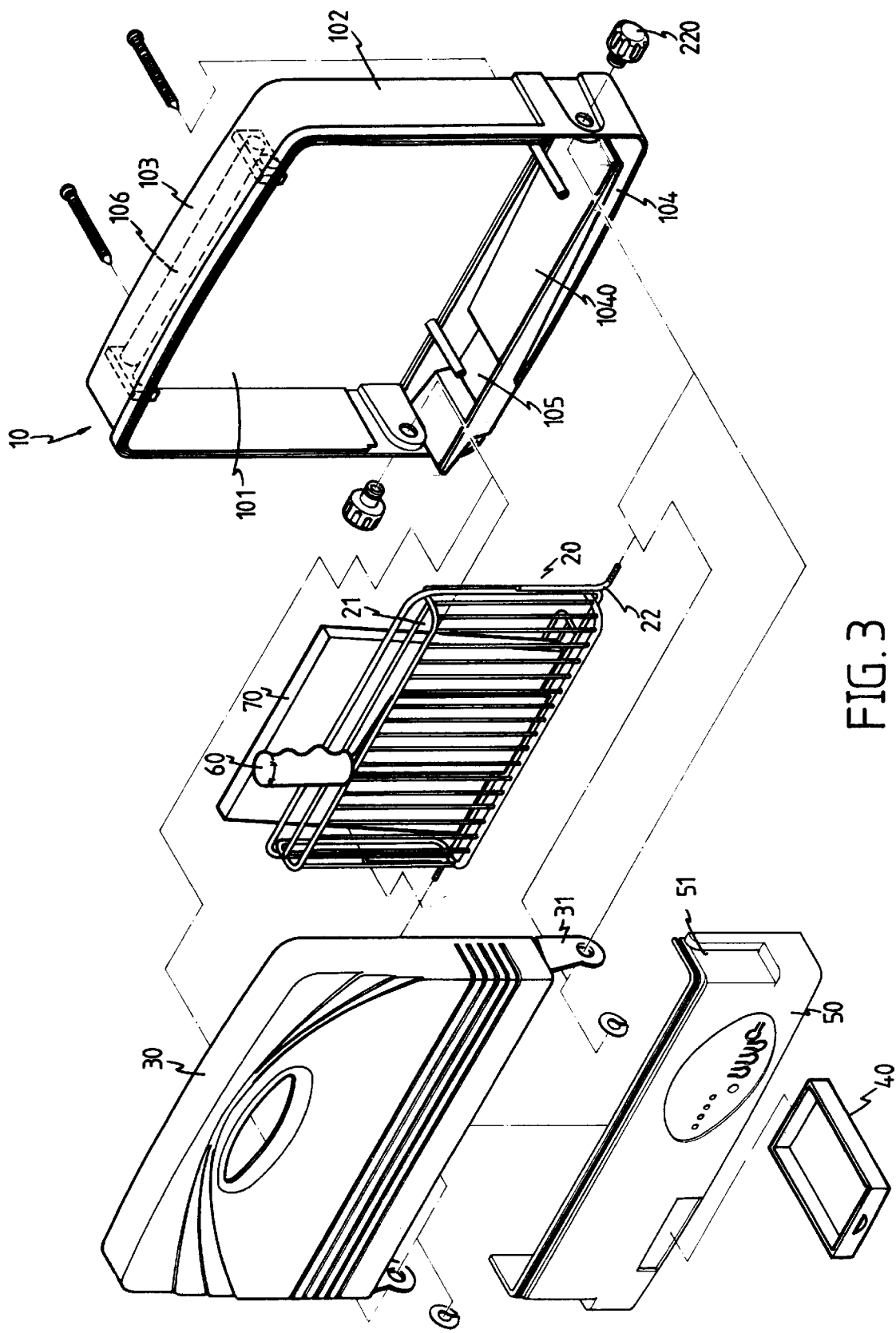
FIG. 3 is an exploded view of the retainer in accordance with the present invention.

Referring to FIGS. 1 to 3, the retainer in accordance with the present invention comprises a base (10) having a bottom (101) with a top plate (103) and a lower plate (104) respectively extending laterally from two opposite sides thereof, and two side plates (102) respectively extending laterally from the other opposite sides of the base (10). An outlet (105) is defined through the lower plate (104) and the lower plate (104) has two inclined surfaces (1040) defined in the inside thereof to let the outlet (105) be located between the two inclined surface (1040). A sanitizing bulb (106) such as an ultraviolet bulb is attached to the inside of the top plate (103) and a rack (20) is connected to the bottom (101) of the base (10), wherein the rack (20) has a plurality of slots (21) defined therein so as to receive the knives (60) (only one is shown) and cutting boards (70) (only one is shown). A collection box (40) is connected to the lower plate (104) and communicates with the outlet (105). Two rods (107) extend from the bottom (101) and the rack (20) is securely supported by the two rods (107). The rack (20) has two shafts (22) extend from two ends thereof.

A first cover (30) has two lugs (31) extending therefrom and the two lugs (31) are pivotally connected to the two side plates (102) of the base (10). The two shafts (22) of the rack (20) extend through the two lugs (31) and the two side plates (102), and two knobs (220) are fixedly connected to the two shafts (22) from the outside of the two side plates (102).

A second cover (50) is connected to the base (10) and located below the first cover (30) wherein the second cover (50) has two slots (51) defined in the top edge of the two ends thereof so that the two lugs (31) are movably received in the two slots (51) when the first cover (30) is pivoted relative to the base (10). When the first cover (30) is pivoted away from the base (10) with the two lug (31) being received in the two slots (51) of the second cover (50), the outside of the first cover (30) is rested on the top edge of the second cover (50) so that the first cover (30) can only be opened to a predetermined angle relative to the base (10).

The sanitizing bulb (106) adopting the ultraviolet bulb has a predetermined length of waves so as to effective destroy the germs to let the knives (60) and the cutting boards (70) meet a standard sanitary requirements.

The invention is not limited to the above embodiment but various modification thereof may be made. It will be understood by those skilled in the art that various changes in form and detail may made without departing from the scope and spirit of the present invention.

What is claimed is:

1. A retainer comprising:

a base (10) having a bottom (101) with a top plate (103) and a lower plate (104) respectively extending laterally from two opposite sides of said bottom (101) and two side plates (102) respectively extending laterally from the other opposite sides of said base (10), a sanitizing bulb (106) attached to the inside of said top plate (103) and an outlet (105) defined through said lower plate (104);

a rack (20) connected to said bottom (101) of said base (10) and having a plurality of slots (21) defined therein;

a first cover (30) pivotally connected to said base (10), and a collection box (40) connected to the lower plate (104) and communicating with said outlet (105).

2. The retainer as claimed in claim 1, wherein said lower plate (104) has two inclined surfaces (1040) defined in the inside thereof and said outlet (105) is located between said two inclined surface (1040).

3. The retainer as claimed in claim 1, wherein said first cover (30) has two lugs (31) extending therefrom and said two lugs (31) are pivotally connected to said two side plates (102) of said base (10).

4. The retainer as claimed in claim 1 further comprising a second cover (50) connected to said base (10) and located below said first cover (30).

5. The retainer as claimed in claim 4, wherein said second cover (50) has two slots (51) defined in two ends thereof so that said two lugs (31) are movably received in said two slots (51) when said first cover (30) is pivoted relative to said base (10).

6. The retainer as claimed in claim 1, wherein said rack (20) has two shafts (22) extending from two ends thereof and said two shafts (22) extend through said two lugs (31) and said two side plates (102).

7. The retainer as claimed in claim 1 further comprising two rods (107) extending from said bottom (101) and said rack (20) is securely supported by said two rods (107).

* * * * *